United States Patent
Shah et al.

(10) Patent No.: US 7,544,352 B2
(45) Date of Patent: Jun. 9, 2009

(54) COSMETIC POWDER COMPOSITION WITH IMPROVED MOISTURIZATION PROPERTIES AND PROCESS FOR MAKING AND USING SAME

(75) Inventors: Arvind Shah, Suffern, NY (US); Ernest Curtis, Milford, PA (US)

(73) Assignee: Avon Products, Inc, New York, NY (US)

( * ) Notice: Subject to any disclaimer, the term of this patent is extended or adjusted under 35 U.S.C. 154(b) by 877 days.

(21) Appl. No.: 10/323,694

(22) Filed: Dec. 19, 2002

(65) Prior Publication Data

US 2004/0120913 A1    Jun. 24, 2004

(51) Int. Cl.
*A61Q 1/12* (2006.01)
(52) U.S. Cl. .......................................... 424/69; 424/401
(58) Field of Classification Search .................. None
See application file for complete search history.

(56) References Cited

U.S. PATENT DOCUMENTS 5,747,049 A * 5/1998 Tominaga .................... 424/401

6,482,441 B1   11/2002   Hasegawa et al. ........... 424/490

FOREIGN PATENT DOCUMENTS

EP         1116753       7/2001
JP         02 247109     10/1990

OTHER PUBLICATIONS

Brochure for Thalasphere HA, Sep. 21, 2000.*
Brochure for Bioetica Inc. Thalasphere HA For Anhydrous Preparations, May 31, 2001.
Brochure for Barnet Products Corp. Levsphere 100G—Preliminary Report, Aug. 12, 1999.
Material Safety Data Sheet for Barnet Products Corp.
European Search Report dated Nov. 21, 2005.

* cited by examiner

*Primary Examiner*—Jyothsna A Venkat
(74) *Attorney, Agent, or Firm*—Joan M. McGillycuddy; Charles J. Zeller; Anthony M. Santini

(57) ABSTRACT

A cosmetic powder composition is provided for retarding moisture loss from skin to which the powder is applied. The cosmetic powder composition has a moisturizer coated filler powder and a time release moisturizing agent. The invention also provides a method for preparing such a cosmetic powder composition that retards moisture loss when applied to the skin and for the use of such cosmetic powder composition to inhibit moisture loss when applied to the skin.

15 Claims, No Drawings

COSMETIC POWDER COMPOSITION WITH IMPROVED MOISTURIZATION PROPERTIES AND PROCESS FOR MAKING AND USING SAME

BACKGROUND OF THE INVENTION

1. Field of the Invention

The present invention relates to cosmetic powder compositions. More particularly, the present invention relates to cosmetic powder compositions having improved skin moisturization properties. Still more particularly, the present invention relates to cosmetic powder compositions that inhibit, reduce, retard, or prevent extended moisture loss from skin when the cosmetic powder composition is applied to the skin. Additionally, the present invention relates to a process for preparing such compositions and the application of such compositions to the skin.

2. Description of the Related Art

Cosmetic powders have been long known and commercially available in both loose and pressed powder form. While both forms of cosmetic powder compositions have been used for a variety of uses by application to the face, lips, around the eyes, nails, scalp and other body locations, many of these powders have suffered from the drawback that they cause drying of or moisture loss from the skin to which they have been applied. As one approach to solve this problem with cosmetic powders, the use of powders physically coated with moisturizing agents, such as for example, the use of glycerin coated talc or mica has been tried. However, this approach has not led to success. Rather, such cosmetic powders, after evidencing a slight lessening of degree of moisture loss in the initial hour or two following application of the cosmetic powder to the skin, that effect is very short lived and after several hours increased moisture loss from the skin is again experienced.

Thus, it would be desirable if a cosmetic powder composition would be provided that has an effect of reducing, inhibiting or preventing moisture loss from the skin for an extended period of time, such as for example up to six hours or more, following application of the cosmetic powder to the skin.

SUMMARY OF THE INVENTION

The invention provides cosmetic powder compositions having improved moisturizing properties when applied to the skin by providing such cosmetic powder compositions having a moisturizer coated filler powder and a time release moisturizing agent in the composition. Such compositions inhibit or retard moisture loss of the skin for an extended period of time following application of the cosmetic powder compositions to the skin. The compositions can, in fact, provide moisturization to the skin so that the moisture level of the skin is not decreased or not significantly decreased over an extended period of up to six hours or more following application of the cosmetic powder to the skin.

DETAILED DESCRIPTION OF THE INVENTION

It has surprisingly been found that when a cosmetic powder composition is provided that has both a moisturizer coated filler powder and a time release moisturizing agent present in the composition, the cosmetic powder composition exhibits a reduced or inhibited tendency to produce loss of moisture from the skin to which the powder composition is applied. The cosmetic powder compositions of this invention provide a non-drying powder to the skin. The compositions of this invention deliver essentially continuous moisturization to the skin instead of producing a moisture loss or drying of the skin that has resulted from essentially continuous absorption of moisture from the skin with prior art cosmetic powder compositions. Thus, the cosmetic powder compositions of this invention are non-drying, provide immediate and long term moisturization of the skin to which they are applied and result in a long term moisturized, naturally healthy looking skin appearance.

The cosmetic powder compositions of this invention may be either free flowing, loose powder compositions or pressed powder compositions, but are preferably pressed power cosmetic compositions. The cosmetic powder composition of this invention may be any suitable cosmetic powder composition for application to any suitable area of skin, such as for application to the face, lips, nose, around the eye, the scalp, or any other suitable body area. The cosmetic powder compositions of this invention also possess excellent sebum/oil absorption properties while inhibiting, retarding, or essentially eliminating moisture loss from the skin to which the cosmetic powder compositions of this invention are applied.

The moisturizer coated (physically coated) filler powder for use in the compositions of this invention can be any suitable moisturizing agent coated filler powder. The moisturizing agent can be for example, glycerin, hyaluronic acid or a salt thereof, an aliphatic hydrocarbon such as for example mineral oil, a silicone oil, or any combinations thereof.

Filler powders that can be physically or chemically coated with a moisturizing agent and used in the compositions of this invention include, but are not limited to, mineral silicate, starch, kaolin, nylon, zinc oxide, titanium oxide, precipitated calcium carbonate, synthetic polymer powder, as well as other fillers known in the art, or any combinations thereof. The fillers may have hydrophobic or hydrophilic surfaces.

The most preferred fillers are mineral silicates, such as mica and talc. When the mineral silicate is mica, it is preferably provided in the form of flakes. Each flake has a size ranging from about 2 μm to about 200 μm, and preferably from about 5 μm to about 70 μm. The thickness of each flake ranges from about 0.1 μm to about 5 μm, and more preferably from about 0.2 μm to about 3 μm. The mica can be of natural origin (for example, muscovite, margarite, rescolithe, lipidolithe, biotite), or synthetic origin. Preferably, the mica is substantially transparent and imparts to the skin a satin-like appearance. In the cosmetic compositions of the present invention, mica filler is present in an amount preferably about 0.1 wt % to about 70 wt %, more preferably about 0.1 wt % to about 50 wt %, and most preferably about 1 wt % to about 10 wt %, based on the total weight of the composition.

When the filler includes talc, the talc may be present in an amount about 0.1 wt % to about 99 wt %, preferably about 10 wt % to about 50 wt %, and more preferably about 20 wt % to about 35 wt %, based on the total weight of the composition. Preferably, the average particle size of the talc filler should range from about 0.5 microns to about 9 microns, and more preferably from about 4 microns to about 8 microns.

Other preferred mineral silicates that can be used in the present invention are phyllosilicates and tectosilicates including, for example pyrophyllite; chlorite; chrysotile; antigorite; lizardite; kaolinite; dickite; nacrite; halloysite; montmorillonite; nontronite; saponite; sauconite; and bentonite; natrolites such as natrolite, nesolite, scolecite, and thomsonite; heulandites such as heulandite, stilbite, and epistibite; zeolites such as analcite, harmotone, phillipsite, chabazite, and gmelinite; or any combinations thereof.

Another preferred filler is a synthetic polymer powder. Such powders include, but are not limited to, polyethylene, polyester (for example, polyethylene isophthalate or terephthalate), N-lauryl lysine, polyamide (for example, nylon), or any combinations thereof. The particles of these powders typically have a size of less than about 50 μm. Also, the particles possess feel-modifying/rolling/slip properties that impart to the skin a velvety feel. Preferably, the synthetic polymer powder filler is present in an amount about 1 wt % to about 40 wt %, and more preferably about 5 wt % to about 25 wt %, based on the total weight of the composition.

As an example of such a coated filler powder useful in the process of this invention there may be mentioned glycerin coated talc, such as Product GI-60746 glycerin coated talc available from Color Techniques, Inc. The time release moisturizing agent component of the composition of this invention can be any suitable time release moisturizing agent, preferably one that releases its moisturizing agent over an extended period of time of 3 or more hours, more preferably over a period of six or more hours following application of the cosmetic composition to the skin. Such a time or sustained release moisturizing agent includes, but is not limited to, one or more moisturizing agents that are entrapped in a substrate, chemically bound to a substrate, and/or encapsulated in substrates or environments. The moisturizing agent that is in a time release form may be any suitable moisturizing agent, including but not limited to, glycerin, hyaluronic acid or a salt thereof, an aliphatic hydrocarbon such as mineral oil, a silicone oil, or any combinations thereof.

As examples of such time or sustained release moisturizing components useful in the composition of this invention there may be mentioned for example, the following:

a multilamellar vesicle encapsulated moisturizing agent, such as a multilamellar vesicle encapsulated glycerin or hyaluronic acid or a salt thereof;

sucrose distearate encapsulated moisturizing agent, such as sucrose distearate encapsulated glycerin or hyaluronic acid or salt thereof, available from Barnet Products Corp. as Levsphere 100G™; and Levsphere 200H ™;

microspheres based on marine crosslinked protein and glycosaminoglycan encapsulated moisturizing agents, such as microspheres of a silicone oil like phenyl trimethicone in marine atelocollagen and marine chondroitin, available as Thalasphere™ from Coletica, Inc.;

a block copolymer encapsulated moisturizing agent, particularly ethylene mixed block copolymer with moisturizing agent entrapped within the block copolymer, such as for example, hyaluronic acid or a salt thereof entrapped in a ethylene mixed blocked copolymer, available as Phytosphere™ from Coletica, Inc.; and a moisturizer chemically bound to a substrate.

Also useful, but not as preferred, are liposome bound moisturizing agents and moisturizing agent chemically bound to a substrate in such a manner that the moisturizer is released over an extended period of time.

The sustained or time release moisturizing agent component of the compositions of this invention will generally be present in the cosmetic powder compositions in an amount 0.1 to about 10 wt %, preferably from about 0.5 to about 7 wt %, and more preferably in an amount of from about 1 to about 6 wt %, based on the total weight of the composition.

The cosmetic powder compositions of this invention may also have present in the composition a metallic soap to impart an unctuous feel and facilitate the adherence of the composition to the skin. Metallic soaps may be derived from one or more organic carboxylic acids having 8 to 22 carbon atoms. Preferably, the organic carboxylic acid has 12 to 18 carbon atoms. Useful examples of such metallic soaps include, but are not limited to, zinc stearate, magnesium stearate, lithium stearate, zinc laurate, magnesium myristate, or any combinations thereof. These soaps are present generally in the form of particles having a size less than 10 μm. The metallic soaps are preferably present in an amount about 1 wt % to about 10 wt %, and more preferably about 2 wt % to about 7.5 wt %, based on the total weight of the composition.

The present compositions may also have present a pigment, such as mineral and/or organic pigments. (such as US FDA-certified color-additive lakes). Although the present invention can accommodate variations in amount of pigment to provide a desired shade, the pigment is typically present from about 0.1 wt % to about 15 wt % based on the total weight of the composition.

Representative mineral pigments include, for example, titanium dioxide (rutile or anatase) optionally surface treated and listed in the Color Index under reference CI 77891; black, yellow, red and brown iron oxides listed in Color Index under references CI 77499, 77492 and 77491; manganese violet (CI 77742); ultramarine blue (CI 77007); chromium oxide (CI 77288); hydrated chromium oxide (CI 77289); ferric blue (CI 77510), or any combinations thereof.

Other exemplary pigments are white nacreous pigments, such as mica covered with titanium oxide, bismuth oxychloride; and colored nacreous pigments, such as titanium mica with iron oxides, titanium mica with ferric blue or chromium oxide, titanium mica with an organic pigment of the aforementioned type, as well as those based on bismuth oxychloride.

Additional exemplary pigments include, for example, the following: D&C Red No. 6 (CI 15850:2); D&C Red No. 7 (CI 15850:1); D&C Red No. 9 (CI 15585); D&C Red No. 13 (CI 15630); D&C Red No. 19 (CI 45170); D&C Red No. 19 (CI 73360); D&C Red No. 19 (CI 45430); D&C Red No. 21 (CI 45380); D&C Red No. 27 (CI 45410); D&C Red No. 36 (CI 12085); D&C Orange No. 4 (CI 15510); D&C Orange No. 5 (CI 45370); D&C Yellow No. 5 (CI 19140); D&C Yellow No. 19 (CI 15985); D&C Orange No. 10 (CI 45475); and carmine lakes (CI 75470); FD&C Red #40 (CI# 16035); FD&C Blue #1 (CI# 42090); FD&C Yellow #5 (CI# 19140); or any combinations thereof.

The pressed cosmetic powder compositions may optionally also have present an inorganic salt. Inorganic salts provide binding properties with less glazing in the final pressed powder composition. Inorganic salts that can be used in the compositions of the present invention include those inorganic salts listed at pages 829 through 830 of the Third Edition of the International Cosmetic Ingredient Handbook (1995), which is incorporated herein by reference. The preferred salts for use in the present compositions include, but are not limited to, calcium carbonate, calcium chloride, calcium phosphate, calcium silicate, calcium sulfate, or any combinations thereof. The inorganic salt, if present, will generally be present in an amount about 0.1 to about 5 wt % based on the total weight of the composition.

The present composition may optionally have synthetic polymer powders (including salts), which provide a nice "payoff" and a silky, luxurious feel on the skin.

Such synthetic polymers include, but are not limited to, those listed at pages 850 through 852 of the Third Edition of the International Cosmetic Ingredient Handbook (1995), which is incorporated herein by reference, except acrylic acid/acrylonite copolymer, adipic acid/CHDM/MA/Neopentyl Glycol/trimellitic anhydride copolymer, adipic acid/diethylene glycol/glycerin crosspolymer, adipic acid/diethylenetriamine copolymer, adipic acid/dimethylaminohydroxypropyl diethylenetriamine copolymer, adipic acid/epoxypropyl diethylenetriamine copolymer, adipic acid/fumaric acid/phthalic acid/twistanedimethanol copolymer, adipic acid/isophthalic acid/neopentyl glycol/trimethylolpropane copolymer, allyl stearate/VA copolymer, aminoethylacrylate phosphate/acrylates copolymer, aminopropyl dimethicone, ammonium acrylates/acrylonitrogens copolymer, ammonium acrylates copolymer, ammonium polyacrylate, and ammonium styrene/acrylates copolymer. Preferably, the synthetic polymers include acrylamide/ammonium acrylate copolymer, acrylamides/acrylates/DMAPA/methoxy PEG methacrylate copolymer, acrylamides copolymer, acrylamide/sodium acrylate copolymer, acrylamidopropyltrimonium chloride/acrylamide copolymer, acrylamidopropyltrimonium choloride/acrylates copolymer, acrylates/acetoacetoxyethyl methacrylate copolymer, acrylates/acetoacetoxyethyl methacrylate copolymer, acrylates/acrylamide copolymer, acrylates/ammonium methacrylate copolymer, acrylates copolymer, acrylates/hydroxyesters acrylates copolymer, acrylates/octylacrylamide copolymer, acrylates/PVP copolymer, acrylates/steareth-50 acrylate copolymer, acrylates/steareth-20 methacrylate copolymer, acrylates/VA copolymer, acrylates/VA crosspolymer, acrylates/vinyl isodecanoate crosspolymer, ethyllene/acrylic acid copolymer, ethylene/acrylic acid/VA copolymer, ethylene/MA copolymer, ethylene/VA copolymer, nylon-6, nylon-11, nylon-12, nylon-66, methacrylate copolymer, polymethyl methacrylate, or any combinations thereof. Such synthetic polymer powders, if present, will generally be present in an amount about 0.1 to about 10 wt % based on the total weight of the composition.

The pressed powder compositions of the present invention also include a liquid binder phase. The term "liquid binder phase" means binder phases that are liquid at room temperature, or at any point in the manufacturing process. The liquid binder phase may include, but is not limited to, one or more oils, hydrocarbons, liquid synthetic esters, silicone oils, waxes, or silicone emulsifiers, and may be an "oil phase". The liquid binder phase is about 1 wt % to about 20 wt %, more preferably about 2 wt % to about 10 wt %, and most preferably about 3 wt % to about 8 wt %, based on the total weight of the composition. For the pressed powder compositions of this invention, the time release moisturizing component is generally added to the composition as part of this liquid binder phase.

The liquid binder phase may have one or more surfactants and emulsifying agents to provide uniformity to the liquid binder phase and/or to maximize pigment color performance. Surfactants and emulsifying agents that may be used in the present compositions include, but are not limited to, those listed at pages 919 and 923 of the Third Edition of the International Cosmetic Ingredient Handbook (1995), which is incorporated herein by reference, except PEG-9 stearate through poloxamine 1504 and polysorbate 20 through PPG-20-buteth-30. The preferred surfactants/emulsifying agents are cetyl dimethicone copolyol, cetyl glyceryl ether/glycerin copolymer, polygylceryl-3 diisostearate, or any combinations thereof.

The liquid binder phase may also include silicones and silanes. Silicones and silanes are feel-modifiers. They improve slip, improve wear and provide moisturization benefits. Silicones and silanes that can be used in the present compositions include, but are not limited to, those listed at pages 844 through 845 of the Third Edition of the International Cosmetic Ingredient Handbook (1995), which is incorporated herein by reference. The preferred silicones/silanes are dimethicone, trimethylsiloxysilicate, or any combination thereof. The most preferred silicone/silane is DOW CORNING 593 FLUID.

The liquid binder phase may also have an ester as a cosolubilizer and/or cosolvent to assist in dissolving solid resins and/or elastomers. Esters that may be used in the present compositions include, but are not limited to, those listed at pages 813 through 818 of the Third Edition of the International Cosmetic Ingredient Handbook (1995), which is incorporated herein by reference. The preferred esters are pentaerythrityl dioleate, pentaerythrityl distearate, pentaerythrityl hydrogenated rosinate, pentaerythrityl isostearate/caprate/caprylate/adipate, pentaerythrityl rosinate, pentaerythrityl stearate, pentaerythrityl stearate/caprate/caprylate adipate, pentaerythrityl tetraabietate, pentaerythrityl tetraacetate, pentaerythrityl tetrabehenate, pentaerythrityl tetrabenzoate, pentaerythrityl tetracaprylate/tetracaprate, pentaerythrityl tetracocoate, pentaerythrityl tetraisononanoate, pentaerythrityl tetraisostearate, pentaerythrityl tetralaurate, pentaerythrityl tetramyristate, pentaerythrityl tetraoleate, pentaerythrityl tetraperlargonate, pentaerythrityl tetrastearate, pentaerythrityl trioleate, or any combinations thereof. Pentaerythrityl tetraoctanoate is a most preferred ester.

The liquid binder phase may also include a hydrocarbon, preferably as an emollient and/or conditioning agent. Hydrocarbons that may be used in the present compositions include those listed at page 827 of the Third Edition of the International Cosmetic Ingredient Handbook (1995), which is incorporated herein by reference, except azulene, butane, C10–13 alkane, C14–17 alkane, coal tar cyclohexane, p-cymene, deodorized kerosene, didecene, dicetylcyclohexane, dipentene, diphenylmethane, ethane, gualazulene, heptane, hexane, isobutane, mineral spirits, mixed terpened, nitromethane, pentane, pristane, propane, red-petrolatum, toluene, turpentine and xylene, or any combinations thereof. Squalane is a preferred hydrocarbon. Such emollient or conditioning agent, if present, will generally be present in an amount about 0.1 to about 5 wt % based on the total weight of the composition.

The pressed powder compositions of the present invention can be used to deliver any type of cosmetic ingredient, e.g., fragrances, color, and biological additives to provide skin benefits or treatment benefits. Useful biological additives include those listed at pages 865 through 870 of the Third Edition of the International Cosmetic Ingredient Handbook (1995), which is incorporated herein by reference. Moreover, by using the pigments and/or colorants discussed above, compositions of the present invention can be formulated to produce a variety of color cosmetic compositions suitable for use on the face, lips, eyes and body. As can be determined by those in the art, any optional ingredient/additive should be added to the phase, either dry powder phase or oil binder phase, with which it is most compatible.

When the cosmetic powder composition is a free flowing powder composition, the ingredients are all mixed together to form the free flowing powder in any suitable manner.

When a cosmetic power composition of this invention is in the preferred pressed power form, the product may be formed in the following manner. The dry powder phase and the liquid binder phase are prepared separately. All powder particulate ingredients are mixed to form a dry powder phase. Preferably, the dry powder phase is mixed until uniform. Suitable mixers/blenders are available and are known by those skilled in the art. The powder composition may also be jet milled by techniques and procedures known in the art.

In a separate vessel, the liquid binder (or oil) phase is prepared either simultaneously, before or after the preparation of the dry powder phase. The liquid binder phase ingredients are mixed, preferably at a temperature about 75 to about 80° F. when the ingredients in the liquid binder phase are liquid at room temperature, but preferably the liquid binder phase is indexed at a temperature about 175 to about 180° F. when the liquid binder phase includes solid ingredients, such as wax.

The liquid binder phase is then added slowly to the dry powder phase. Both phases are mixed, preferably in an Oysterizer™ at a high speed, until blended. The blended mixture is then preferably sifted through a sieve. One example of a suitable sieve is USA standard testing sieve/screen no. 35 having an opening number 020 (i.e., 550 micrometer/0.0197 inches).

After the liquid and powder phases have been blended and, preferably, sifted, pressing occurs in the range about 800 psi (gauge pressure) to about 2500 psi.

Preferably, pressing of the mixture of ingredients takes place in the range about 1000 psi to about 1700 psi. The pressure ranges result in the formation of a pressed composition having excellent aesthetic appearance, superior binding, and superior slip with creamy and moist application.

The following are exemplary, but not limiting, examples of cosmetic powder compositions of this invention.

Each of the two following pressed powder compositions of the invention were prepared according the general procedure mentioned hereinbefore.

EXAMPLE 1

Dry Powder Phase

| Component | Wt % |
| --- | --- |
| Glycerin coated sheer talc | 15 |
| Glycerin coated jet milled talc | 15 |
| Feel modifying agent | 62 |
| Lecithin coated mica | 32.55 |
| Pigment | 1.45 |

Oil Phase

| | |
| --- | --- |
| Levsphere 100G ™ | 1.2 |
| Solubilizing agent | 0.6 |
| Binding agent | 0.6 |
| Diluent | 3.6 |

EXAMPLE 2

Dry Phase

| Component | Wt % |
| --- | --- |
| Glycerin coated talc | 30 |
| Glycerin coated mica | 32.55 |
| Powdered spherical feel modification Agents | 30 |
| Pigments | 0.45 |

Oil Phase

| | |
| --- | --- |
| Levsphere 100G ™ | 1.08 |
| Diluent | 2.88 |
| Solubilizing agent | 0.48 |
| Binding agent | 0.48 |
| Additional moisturizing agent | 1.08 |

In Examples 1 and 2, Levsphere 100G are 1µ multilamellar vesicles encapsulating glycerin, i.e. bilayers of sucrose distearate (30%) and aqueous interfaces containing glycerin (60%).

The improved moisturizing properties of the cosmetic powder compositions of this invention are illustrated by the following comparative example in which the cosmetic powder composition of Example 2 is compared to the commercially available translucent pressed powder product Moisture Whip® of Maybelline, Inc. The comparative testing of the two compositions was done utilizing a Hydrascan instrument that measures Transient Thermal Transfer. Based on thermal waves propagated into the epidermis, transient thermal transfer changes according to tissular humidity. Thus, the Hydrascan instrument is a direct, non-invasive method to quantify the effect of a product on the cutaneous hydration rate and has the capacity to reach three different epidermal depths, namely superior layer of the epidermis, superior and median layers of the epidermis, and the entire epidermis.

In the test, panelists reported to the lab the day of the study and were required to remain in a climate controlled room throughout the length of the study (RH % 40–60, Temp. 24±2° C.). The controlled study consisted of one application (2 mg/cm$^2$) of the product to the inner forearm of the panelists using a fingercot. The comparative test results are set forth in Table 1. The test data demonstrates that both cosmetic powder compositions experience an initial loss of moisture shortly (1 hr) after the powder is applied to the skin, although the powder composition of the invention produces a lower % moisture loss. Similarly, after three hours post application both powder compositions produce a reduction in % moisture loss indicating an initial moisturization action by both products. However, the commercially available prior art product then again produces an increased moisture loss (i.e., loses it moisturization effect), whereas the powder composition of the invention continues to reduce the % moisture loss, i.e. produces moisturization of the skin as shown by the data at six hours post application.

TABLE 1

| Epidermis Test Layer | Post Application Time (hrs) | Moisture Loss (%) for Example 2 Powder (Invention) | Moisture Loss (%) for Moisture Whip ® Powder |
| --- | --- | --- | --- |
| Superior layers of epidermis | 1 | −11 | −15 |
| Superior layers of epidermis | 3 | −6 | −8 |
| Superior layers of epidermis | 6 | −7 | −13 |
| Superior layers of epidermis | 1 | −9 | −13 |
| Superior layers of epidermis | 3 | −4 | −6 |
| Superior layers of epidermis | 6 | −2 | −9 |
| Entire epidermis | 1 | −7 | −11 |
| Entire epidermis | 3 | −1 | −5 |
| Entire epidermis | 6 | 0 | −6 |

While the present invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A cosmetic powder composition comprising a moisturizer coated filler powder and a time release moisturizing agent, wherein the moisturizer coated filler powder has surfaces, and wherein the time release moisturizing agent is at the surfaces of the moisturizer coated filler powder wherein the time release moisturizing agent is selected from the group consisting of microsphere of phenyl trimethicone in marine atelocollagen and marine chondroitin; sucrose distearate encapsulated glycerin; sucrose distearate encapsulated hyaluronic acid and a salt of sucrose distearate encapsulated hyaluronic acid wherein the time release moisturizing agent is present in an amount about 0.1 wt% to about 10 wt% based on the total weight of the composition.

2. The cosmetic powder composition of claim 1, wherein the time release moisturizing agent is present in an amount about 0.5 wt% to about 7 wt% based on the total weight of the composition.

3. The cosmetic powder composition of claim 1, wherein the time release moisturizing agent is present in an amount about 1 wt% to about 6 wt% based on the total weight of the composition.

4. The cosmetic powder composition of claim 1, wherein the filler powder comprises a filler powder selected from the group consisting of talc and mica.

5. The cosmetic powder composition of claim 4, wherein the talc is glycerin coated.

6. The cosmetic powder composition of claim 1, wherein the cosmetic powder composition is a pressed cosmetic powder composition.

7. A process for producing a cosmetic powder comprising providing a moisturizer coated filler powder having surfaces thereon and adding a time release moisturizing agent to the surfaces of the moisturizer coated filler powder wherein the time release moisturizing agent is selected from the group consisting of microsphere of phenyl trimethicone in marine atelocollagen and marine chondroitin; sucrose distearate encapsulated glycerin; sucrose distearate encapsulated hyaluronic acid and a salt of sucrose distearate encapsulated hyaluronic acid wherein the time release moisturizing agent is present in an amount about 0.1 wt% to about 10 wt% based on the total weight of the composition.

8. The process of claim 7, wherein the cosmetic powder composition is a pressed cosmetic powder composition and the time release moisturizing agent is part of an oil phase added to the surfaces of the moisturizer coated filler powder.

9. A method for inhibiting the moisture loss effect of a cosmetic powder on the skin comprising applying to the skin a cosmetic powder composition having a moisturizer coated filler powder having surfaces thereon and a time release moisturizing agent at the surfaces of the moisturizer coated filler powder wherein the time release moisturizing agent is selected from the group consisting of microsphere of phenyl trimethicone in marine atelocollagen and marine chondroitin; sucrose distearate encapsulated glycerin; sucrose distearate encapsulated hyaluronic acid and a salt of sucrose distearate encapsulated hyaluronic acid wherein the time release moisturizing agent is present in an amount about 0.1 wt% to about 10 wt% based on the total weight of the composition.

10. The method of claim 9, wherein the time release moisturizing agent is present in an amount about 0.5 wt% to about 7 wt% based on the total weight of the composition.

11. The method of claim 9, wherein the time release moisturizing agent is present in an amount about 1 wt% to about 6 wt% based on the total weight of the composition.

12. The method of claim 9, wherein the filler powder comprises a filler selected from the group consisting of talc and mica.

13. The method of claim 12, wherein the filler powder comprises a glycerin coated talc.

14. The method of claim 9, wherein the cosmetic powder composition is a pressed cosmetic powder composition.

15. The method of claim 9, wherein the cosmetic powder composition inhibits moisture loss for at least 3 to 6 hours after its application to the skin.

* * * * *